(12) United States Patent
Archie et al.

(10) Patent No.: US 7,094,616 B2
(45) Date of Patent: Aug. 22, 2006

(54) HIGH RESOLUTION CROSS-SECTIONING OF POLYSILICON FEATURES WITH A DUAL BEAM TOOL

(75) Inventors: Charles N. Archie, Granite Springs, NY (US); Wei Lu, Poughkeepsie, NY (US); Chester Wasik, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 175 days.

(21) Appl. No.: 10/708,452

(22) Filed: Mar. 4, 2004

(65) Prior Publication Data

US 2005/0196880 A1    Sep. 8, 2005

(51) Int. Cl.
*H01L 21/66* (2006.01)
(52) U.S. Cl. ......................................................... 438/14
(58) Field of Classification Search ................ 438/689, 438/687, 676, 14; 250/492
See application file for complete search history.

(56) References Cited

U.S. PATENT DOCUMENTS

| | | | |
|---|---|---|---|
| 4,682,019 A | 7/1987 | Nakatsui et al. | |
| 5,481,109 A | 1/1996 | Ninomiya et al. | |
| 5,612,535 A | 3/1997 | Wang | |
| 5,798,529 A | 8/1998 | Wagner | |
| 5,986,264 A | 11/1999 | Grunewald | |
| 6,268,608 B1 | 7/2001 | Chandler | |
| 6,355,563 B1 * | 3/2002 | Cha et al. | 438/687 |
| 6,454,512 B1 | 9/2002 | Weiss | |
| 6,507,044 B1 | 1/2003 | Santana, Jr. et al. | |
| 6,753,538 B1 * | 6/2004 | Musil et al. | 250/492.2 |
| 2002/0019137 A1 | 2/2002 | Tsung et al. | |
| 2002/0094694 A1 | 7/2002 | Russell et al. | |

* cited by examiner

*Primary Examiner*—Carl Whitehead, Jr.
*Assistant Examiner*—Monica D. Harrison
(74) *Attorney, Agent, or Firm*—Scully, Scott, Murphy & Presser; Joseph P. Abate, Esq.

(57) ABSTRACT

A method for high resolution cross sectioning of polysilicon features with a dual electron (E) beam and focused ion beam. The method comprises consecutive steps of encapsulating the polysilicon features of interest with a metal coating, followed by ion beam cross sectioning of the metal encapsulated polysilicon features, followed by electron (E) beam and gas (XeF2) etching and cleaning of the polysilicon from the encapsulating metal to remove the polysilicon while leaving the polysilicon surface features preserved in the encapsulating metal. The method is practiced with a dual beam tool comprising a scanning electron microscope (SEM) and a focused ion beam tool. Advantageously, in the electron (E) beam and gas etching and cleaning step, the cleaning and imaging are simultaneous, allowing E beam imaging while the cleaning is taking place to evaluate the extent of cleaning. The step of etching and cleaning is followed by scanning electron microscope (SEM) imaging and evaluation of the metal preserved polysilicon features.

16 Claims, 1 Drawing Sheet

HIGH RESOLUTION CROSS-SECTIONING OF POLYSILICON FEATURES WITH A DUAL BEAM TOOL

BACKGROUND OF INVENTION

The present invention relates generally to high resolution cross-sectioning of polysilicon features with a dual beam tool, and more particularly pertains to high resolution cross-sectioning of polysilicon features with a dual beam (electron beam and focused ion beam) tool that provides a compatible metrology technique, provides measurements of iso-features, and provides a metrology for 3-D (three dimensional) profiles.

In current technologies used in process development and failure analysis during semiconductor manufacturing, it is very important to be able to obtain precise measurements and cross sections of critical polysilicon structures, such as polysilicon gate line features, which are developed on a silicon wafer.

The prior art uses an ion beam initiated Pt (platinum) coating on polysilicon line features, takes an ion beam cross-section of the Pt coated polsilicon line features, and then uses SEM (scanning electron microscope) imaging to evaluate the features of the polysilicon line features. The prior art process results in severe rounding of the top edges of the polysilicon line features.

SUMMARY OF INVENTION

The present invention provides high resolution cross-sectioning of polysilicon features with a dual beam (electron beam and focused ion beam) tool, and is particularly applicable to features having dimensions of 90 nm or smaller. The processes of the present invention allow evaluation and measurement of polysilicon features on a silicon wafer by a dual beam tool employing a scanning electron microscope and a focused ion beam tube without destruction or deformation of the polysilicon features by the focused ion beam, as was prevalent with prior art processes.

The advantages of the present invention are that it is a compatible metrology technique, provides measurement of iso-features, and provides a metrology for 3-D (three dimensional) profiles. The present invention also does not damage or deform the features being measured, as is common with prior art approaches using an ion beam during platinum encapsulation of the features being measured which result in severe rounding of the top edges of polysilicon line features.

The method of the present invention comprises consecutive steps of encapsulating the polysilicon features of interest with a metal coating, followed by ion beam cross sectioning of the metal encapsulated polysilicon features, followed by electron (E) beam and gas etching and cleaning of the polysilicon from the encapsulating metal to remove the polysilicon while leaving the polysilicon surface features preserved in the encapsulating metal.

In greater detail, the method is practiced with a dual beam tool comprising a scanning electron microscope (SEM) and a focused ion beam tool. Advantageously, in the electron (E) beam and gas etching and cleaning step, the cleaning and imaging are simultaneous, allowing E beam imaging while the cleaning is taking place to evaluate the extent of cleaning. The step of etching and cleaning is followed by a final scanning electron microscope (SEM) imaging and evaluation of the metal preserved polysilicon features. The step of etching and cleaning preferably utilizes an etching gas comprised of XeF2 (xenon difluoride).

The step of encapsulating preferably includes encapsulating the polysilicon features of interest with an E (electron) beam initiated metal coating wherein the E beam energizes and speeds up metal deposition during the encapsulating step while resulting in minimized damage to the features of interest. The method is advantageously practiced on polysilicon features having dimensions of 90 nm or smaller. The polysilcon features can be encapsulated in any suitable metal such as platinum Pt or tungsten W.

BRIEF DESCRIPTION OF DRAWINGS

The foregoing objects and advantages of the present invention for high resolution cross-sectioning of polysilicon features with a dual beam tool may be more readily understood by one skilled in the art with reference being had to the following detailed description of several embodiments thereof, taken in conjunction with the accompanying drawings in which.

DETAILED DESCRIPTION

As chip design ground rules have been reduced, the gate features on a silicon chip have also become smaller. Moreover, the gate feature profile metrology is critical for proper process control. The only true cross-sectioning technique is by mechanical cleavage, which is destructive and time consuming.

The present invention uses a dual beam tool and system to provide non-whole-wafer-destructive cross-sectioning with a high throughput. The dual beam approach of the present invention preserves the true profile of the polysilicon features being examined and also provides high resolution images for metrology.

Figure 1:
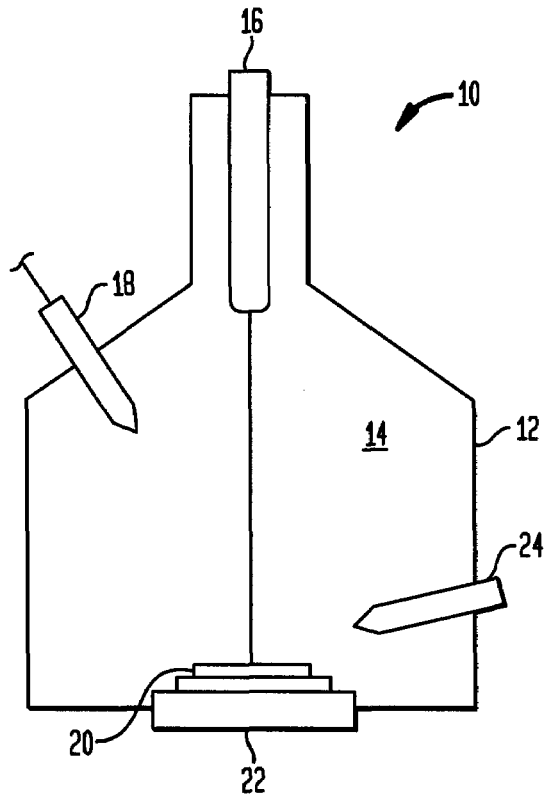
FIG. 1 illustrates a dual beam (electron beam and focused ion beam) tool which is used to obtain high resolution cross-sectioning of polysilicon features pursuant to the present invention to provide measurements of iso-features and a metrology for 3-D (three dimensional) profiles of the polysilicon features.

FIG. 1 illustrates a dual beam (electron beam and focused ion beam) tool 10 which is used to obtain high resolution cross-sectioning of polysilicon features pursuant to the present invention. The dual beam tool 10 includes an enclosure wall of a tool housing 12 that encloses a tool chamber 14. A scanning electron microscope (SEM) 16 extends through the housing wall 12 into the tool chamber 14 at an angle of tilt relative to a focused ion beam (FIB) tube 18 and a horizontal surface of a test specimen 20 mounted on a stage 22. A nozzle 24 of a gas injection system (GIS) also extends through the housing wall 12 into the tool chamber 14, and is adapted to introduce a gas, such as gaseous $XeF_2$, into contact with or in proximity to the sample or test specimen 20.

An exemplary process below mentions a 52° tilt angle which is really a function of a standard configuration of the dual beam tool. Typically, a silicon wafer is milled by the FIB bean with the wafer tilted at an angle which is limited by the configuration of the tool, and the wafer is then rotated to be cleaned and imaged by the SEM bean. The tool configuration limits the maximum tilt angle to about 60 degrees. Preferably, the SEM beam should be aimed at the highest angle possible to obtain the best image relative to the cross-sectioned face.

The first step of the present invention uses an encapsulation procedure to preserve the profile of the polysilicon features being examined, particularly the top surfaces and edges of the polysilcon features. The polysilcon features can be encapsulated in any suitable metals such as platinum Pt or tungsten W or any other suitable metal. The example given herein is with respect to Pt which is exemplary of other metals in general. A local E beam provided by an electron microscope is used in conjunction with the Pt deposition, and minimizes damage to the silicon features compared to the regular prior art deposition using an ion beam.

Figure 2:
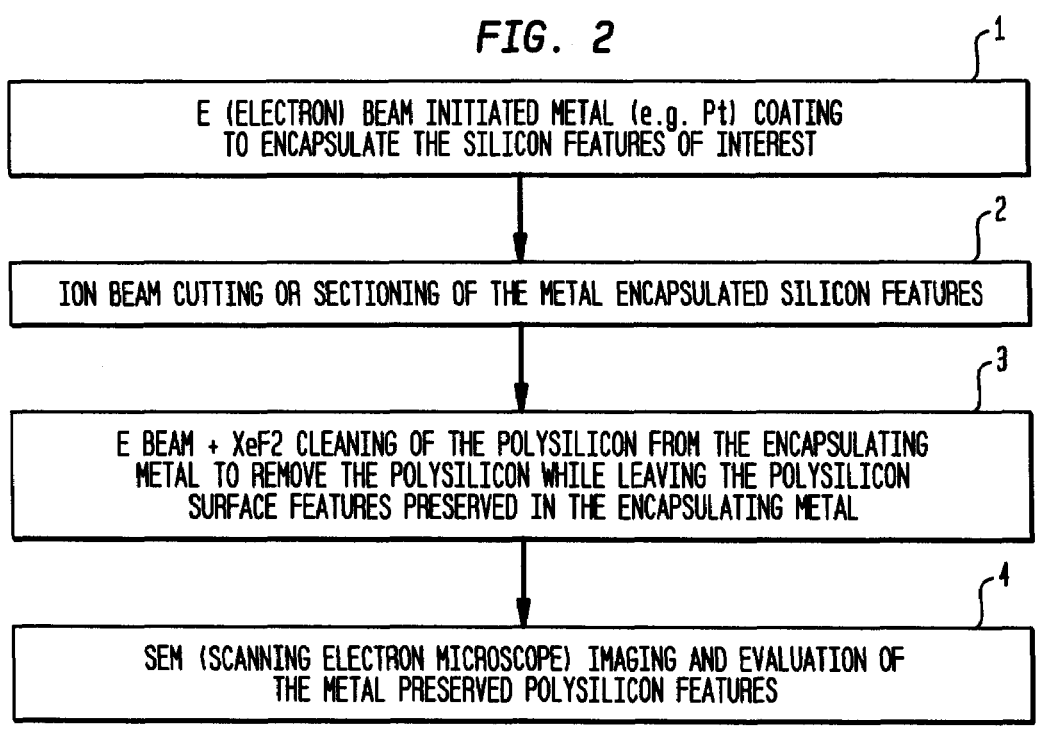
FIG. 2 is a process flow diagram which illustrates the consecutive steps of the present invention for high resolution cross-sectioning of polysilicon features with a dual beam tool.

FIG. 2 is a process flow diagram which illustrates the consecutive steps of the present invention for high resolution cross-sectioning of polysilicon features with a dual beam tool. The process of the subject invention uses consecutive steps of:

(1) E (electron) beam initiated metal (e.g. Pt) coating to encapsulate the silicon features of interest;

(2) ion beam cutting or sectioning of the metal encapsulated silicon features;

(3) E beam and etching gas (preferably XeF2 (xenon bifluoride)) etching/cleaning of the polysilicon from the encapsulating metal to remove the polysilicon while leaving the polysilicon surface features preserved in the encapsulating metal; and (4) SEM (scanning electron microscope) imaging and evaluation of the metal preserved polysilicon features.

The dual beam approach of the present invention uses an E (electron) beam in the first and third steps and an ion beam in the second step. The use of an E beam in the third cleaning step is considered to be particularly advantageous in the process of the present invention. The cleaning step utilizes a selective etching gas, XeF2 (xenon difluoride), with E (electron) beam enhancement to selectively etch the polysilicon to form a sharp polysilicon profile contrast and to provide high resolution images. The E beam energizes the XeF2 gas to speed up the etching process.

One particular exemplary process was carried out and is described below. The exemplary process used an FEI corporation electron microscope and performed the process with the following parameters and conditions.

1. The first step used an electron (E) beam initiated metal (e.g. Pt platinum) coating for encapsulation, which resulted in minimized damage to the tested features by the electron beam. The particular exemplary process used an FEI corporation electron microscope with the following parameters and conditions:

E beam in the range of 500 eV to 3000 eV (electron volts) with a flexible beam current;

beam scanning conditions, (DW(dwell time)=0.2 µs, OL (overlap, where 0 is no or 0% overlap)=0;

beam scanning size=3 µm×2 µm×0.2 µm (length×width×depth), tilt=52°;

precursor, C9H16Pt (Methylcyclopentadienyl platinum, (CH3C5H4)(CH3)Pt) which is a standard gas for the FEI tool, and using a standard gas injection system (GIS) for the FEI tool.

2. The second step used a FIB (focused ion beam) to cut a cross-section through the sample using a standard process for the FEI tool with:

beam scanning conditions, (DW=10 µs, OL=50%);

scanning box size=3 µm×0.8 µm×0.12 µm (depending on feature size);

image mode, cleaning cross section (CCS) which mills a series of advancing lines, beam=10 pA (pico amps).

3. The third step used an E beam and XeF2 gas cleaning on the cross-section cut through the sample:

the E beam slows down the XeF2 gas etching rate relative to the prior art ion beam to provide a more controllable and moderate rate etching process;

cleaning and imaging are simultaneous, allowing E beam imaging while the cleaning is taking place to evaluate the extent of cleaning;

E beam range, 500 eV to 12,000 eV, Tilt=52°;

gas pressure in chamber=$2.3 \times 10^{-6}$ mbar (0 to $1 \times 10^{-4}$ mbar);

precursor gas, XeF2 is delivered by a standard GIS for the FEI tool.

4. The fourth step is SEM (scanning electron microscope) imaging of the silicon surface features preserved in the encapsulating metal.

The present invention uses SEM+XeF2 to etch polysilicon in an in-situ application at a controllable moderate rate for the purpose of delineation of the boundary of polysilicon and the encapsulation metal layer to provide for an accurate metrology measurement of the dimensions of the polysilicon features as preserved in the encapsulating metal.

This is followed by imaging of the tested features with an SEM (scanning electron microscope).

A comparison of the process of the present invention with the process of the prior art demonstrated the following advantages of the present invention.

The damaged edge roundness decreased by 17 nm for the top edge (56% better), and decreased by 12 nm for the bottom edge (44% better). For the present invention, the top-edge roundness can reach an average of 6 nm. The prior art process resulted in a narrower line width, with the difference being worse near the top and bottom edges. The present invention resulted in more vertical sidewall angles. The prior art process did not provide a sharp boundary transition which can cause measurement errors.

A comparison of the present invention with AFM (atomic force microscopy) on the metrology of a polysilicon line from 130 nm ground technology measured seven fields, each with a different line width. The AFM methodology used a ten scan line average as an RMS (reference measurement system), while the present invention used the dual beam methodology as described herein. The data from the AFM and the dual beam methodology are from the same field, but not from the exact same location. The total measurement uncertainty (TMU) was less than 7.4 nm all CDs (critical dimensions) (75% CD, 50% CD, and 10% CD). In summary, the present invention provided an excellent 3D profile.

While several embodiments and variations of the present invention for high resolution cross-sectioning of polysilicon features with a dual beam tool are described in detail herein, it should be apparent that the disclosure and teachings of the present invention will suggest many alternative designs to those skilled in the art.

The invention claimed is:

1. A method for high resolution cross sectioning of polysilicon features with a dual electron (E) beam and focused ion beam, comprising consecutive steps of:

encapsulating the polysilicon features of interest with a metal coating to preserve the profile of the polysilicon features of interest;

ion beam cross sectioning of the metal encapsulated polysilicon features;

electron (E) beam and etching gas etching and cleaning of the polysilicon from the encapsulating metal to remove the polysilicon while leaving the profile of the polysilicon surface features preserved in the encapsulating metal.

2. The method of claim 1, wherein the method is practiced with a dual beam tool comprising an electron (E) beam and focused ion beam tool.

3. The method of claim 1, wherein the method is practiced with a dual beam tool comprising a scanning electron microscope (SEM) and a focused ion beam tool.

4. The method of claim 3, where in the electron (E) beam and etching gas etching and cleaning of the polysilicon from the encapsulating metal, cleaning and imaging are simultaneous, allowing E beam imaging while the cleaning is taking place to evaluate the extent of cleaning.

5. The method of claim 4, wherein the step of etching and cleaning is followed by scanning electron microscope (SEM) imaging and evaluation of the metal preserved polysilicon features.

6. The method of claim 5, wherein the step of etching and cleaning utilizes an etching gas comprised of XeF2 (xenon difluoride).

7. The method of claim 3, wherein the step of etching and cleaning is followed by scanning electron microscope (SEM) imaging and evaluation of the metal preserved polysilicon features.

8. The method of claim 7, wherein the step of etching and cleaning utilizes an etching gas comprised of XeF2 (xenon difluoride).

9. The method of claim 1, wherein the step of encapsulating includes encapsulating the polysilicon features of interest with an E (electron) beam initiated metal coating wherein the E beam energizes and speeds up metal deposition during the encapsulating step while resulting in minimized damage to the features of interest.

10. The method of claim 1, wherein the step of etching and cleaning utilizes an etching gas comprised of XeF2 (xenon difluoride).

11. The method of claim 1, wherein the method is practiced on polysilicon features having dimensions of 90 nm or smaller.

12. The method of claim 1, wherein the method is practiced with a dual beam tool comprising a scanning electron microscope and focused ion beam tool, and the etching and cleaning step is followed by scanning electron microscope (SEM) imaging and evaluation of the metal preserved polysilicon features of interest.

13. The method of claim 1, including encapsulating the polysilicon features in platinum Pt.

14. The method of claim 1, including encapsulating the polysilicon features in tungsten W.

15. A method according to claim 1, comprising the further step of measuring dimensions of the polysilicon features as preserved in the encapsulating metal.

16. A method according to claim 1, wherein:
said polysilicon features include top surfaces and edges of the polysilicon; and
the method comprises the further step of measuring dimensions of the polysilicon features as preserved in the encapsulating metal.

* * * * *